United States Patent
Chen

[11] Patent Number: 5,191,114
[45] Date of Patent: Mar. 2, 1993

[54] PROCESS FOR ENHANCING THE FLOW CHARACTERISTICS OF IBUPROFEN

[75] Inventor: Jivn-Ren Chen, Shreveport, La.

[73] Assignee: Sage Pharmaceuticals, Inc., Shreveport, La.

[21] Appl. No.: 773,258

[22] Filed: Oct. 9, 1991

[51] Int. Cl.$^5$ .......................................... C07C 53/134
[52] U.S. Cl. .................................. 562/496; 427/189; 424/465
[58] Field of Search ................ 562/494, 496; 427/189; 424/80, 465

[56] References Cited

U.S. PATENT DOCUMENTS

| | | | |
|---|---|---|---|
| 4,476,248 | 10/1984 | Jordon | 562/494 |
| 4,690,834 | 9/1987 | Appelgren et al. | 427/189 |
| 4,904,477 | 2/1990 | Ho et al. | 424/465 |
| 4,910,023 | 3/1990 | Botzolakis | 424/470 |
| 4,911,921 | 3/1990 | Denton et al. | 424/80 |
| 4,994,604 | 2/1991 | Tung et al. | 562/401 |

FOREIGN PATENT DOCUMENTS 0172014 12/1985 European Pat. Off. .
0241126 3/1987 European Pat. Off. .

*Primary Examiner*—Paul J. Killos
*Attorney, Agent, or Firm*—John M. Harrison

[57] ABSTRACT

Direct compressible ibuprofen particles are formed by treating commercially available, dry ibuprofen with a hydrophilic solvent in one embodiment, a mixture of a hydrophilic solvent and one or more hydrophobic organic solvents in a second embodiment and one or more hydrophobic organic solvents in a third embodiment, to change at least the external crystalline shape of the ibuprofen from a flow-retarding shape to a free-flowing, easily compressible configuration. A typical hydrophilic solvent is water and among the hydrophobic solvents which may be used are acetone, methyl alcohol, ethyl alcohol, isopropyl and N-propyl alcohol. Direct compressible ibuprofen particles having superior flow characteristics may also be prepared by mixing commercially available, dry ibuprofen with micron size, amorphous silica gel in various formulations.

27 Claims, No Drawings

PROCESS FOR ENHANCING THE FLOW CHARACTERISTICS OF IBUPROFEN

BACKGROUND OF THE INVENTION

1. Field of the Invention

This invention relates to therapeutic agents and more particularly, to pharmaceutical compositions and preparations containing the analgesic and non-steroidal anti-inflammatory compound, ibuprofen. These compositions are extensively used and are of great value in the treatment of pain and inflammation, particularly in reducing discomfort from various types of arthritis. The chemical formulation for ibuprofen is $(\pm)$-2-(P-Isobutylphenyl) propionic acid [Ibuprofen] and S-(+)-2-(p-Isobutylphenyl] propionic acid [S(+)-ibuprofen] and are normally supplied in crystalline form. However, it has been found that crystalline ibuprofen normally received commercially from chemical suppliers cakes easily and exhibits poor flow properties, particularly after storage over a long period of time. Accordingly, when used without any further treatment in tableting and capsule-filling equipment for which acceptable powder flow characteristics are essential to product processing, significant caking and other flow problems may arise, both during transfer of the ibuprofen from one place to another and during the tableting or capsule-filling process. Consequently, it has been found expedient to combine the raw ibuprofen with pharmaceutically acceptable excipients to form granules containing from about 50 to about 90 percent by weight ibuprofen. These granules exhibit much better hardness and free-flowing properties and characteristics than the unmixed, commercially-available crystalline ibuprofen and are more stable over a longer period of time.

It is therefore desirable to formulate ibuprofen particles which exhibit satisfactory free-flowing characteristics in order to more efficiently and expeditiously manufacture ibuprofen tablets and capsules. This objective is achieved in a first embodiment by mixing the commercial grade ibuprofen powder or crystals with a hydrophilic solvent such as hot water. In a second embodiment the ibuprofen is mixed with a mixture of a hydrophilic solvent such as water and one or more hydrophobic solvents, such as acetone, methyl alcohol, ethyl alcohol, isopropyl alcohol and N-propyl alcohol, the latter group of which are miscible with water. In a third embodiment of the invention, the ibuprofen is mixed with one or more of the hydrophobic organic solvents innumerated above, to create a more free-flowing ibuprofen product. The granulating liquid operates in each case to melt or partially dissolve and change the shape of at least the surface crystalline structure of the ibuprofen particles from a flow-retarding, generally rectangular shape to a free-flowing and easily compressible cubic or irregular configuration. In the case of a granulating liquid containing both a hydrophilic and one or more hydrophobic solvents, mixing is conducted at a temperature in the range of from about 20° C. to about 100° C. and the ratio of concentration of the hydrophilic solvent to the hydrophobic solvent may range from 0.5 to 99.5, depending upon the chosen material source, equipment used and process conditions.

In a fourth embodiment of the invention, direct compressible ibuprofen particles having superior dry flow characteristics are prepared by mixing commercially available, dry ibuprofen with micron size amorphous silica gel ($SiO_2$) in a weight percent of from about 0.05 to about 5.0 percent of the weight of the ibuprofen. The silica gel component acts to coat, and therefore minimize adhesion, of the ibuprofen particles, and may be used in any one of several commercially available materials, including "fumed", or synthetic silica or a coagulated aerosol of synthetic silica, in non-exclusive particular.

2. Description of the Prior Art

Various ibuprofen compositions, as well as processes of manufacture and purification, are well known in the art.

European Patent Application No. 0241126, entitled "Therapeutic Agents" details a solid pharmaceutical composition which includes granules consisting of an aggregate of ibuprofen crystals which have advantageous free flowing, compression and formulation properties. The solid composition is essentially non-friable and includes no excipients. However, solid dosage formulations produced by mixing a composition according to the invention with appropriate formulation excipients, may also be prepared. The median crystalline particle size of the crystalline ibuprofen prepared according to the invention is said to be in the range of 5-100 microns and damp ibuprofen is preferred for employment in a wet granulation process to formulate the solid ibuprofen composition.

European Patent Application No. 172014 relates to a granular pharmaceutical composition which includes ibuprofen. The application states that in order to effect effective disintegration of the compacted granules in the dosage forms, the granules must contain an excipient, which is identified as croscarmellose sodium. The granules disclosed contain about 85-99 percent by weight ibuprofen and from about 1 percent to about 15 percent by weight croscarmellose sodium.

Japanese Patent Application No. 120,616 also relates to granular pharmaceutical compositions which include ibuprofen. The patent details a process by which the desired granules may be produced by heat melting ibuprofen powder and subsequently cooling the powder until the melt is solidified, after which the solid melt is crushed into granules. The patent notes that the process is time-consuming, particularly in the cooling stage, wherein the resulting granules are characterized by solid blocks of crystalline ibuprofen.

U.S. Pat. No. 4,690,834, entitled "Process for Coating Solid Particles" details a process for coating solid particles using a material which is highly viscous or solid at room temperature. The coating material and particulate material to be coated are introduced into a mixing disc apparatus, where the coating material forms a finely divided mist for coating the particulate material.

U.S. Pat. No. 4,911,921, entitled "High Ibuprofen Content Granulations", details a granular pharmaceutical composition containing 85-99 percent ibuprofen, 0.9 to about 15.0 percent binder and 0.1 to about 5.0 percent polyvinylpyrrolidone, wherein the polyvinylpyrrolidone defines a film with a portion of the binder to form agglomerates. Ibuprofen may be fluidized with a portion of the binder in a fluid bed apparatus and sprayed with aqueous dispersion of polyvinylpyrrolidone and the remainder of the binder. This granulation may be subsequently blended with additional excipients and, optionally, additional active pharmaceutical ingredients, for direct compression into tablets.

U.S. Pat. No. 4,904,477, entitled "Spray Dried Ibuprofen Compositions", is drawn to a spray dried ibuprofen composition suitable for direct compression into tablets and including a spray dried dispersion in water of ibuprofen, pregalatinized starch, a disintegrate and a wetting agent for the ibuprofen.

U.S. Pat. No. 4,994,604, entitled "Formation and Resolution of Ibuprofen Lysinate; Salt Formation In Aqueous-Organic Solvent Mixture Followed by Preferential Crystallization", details a process for the formation and resolution of (S) ibuprofen-(S) -lysine by preferential crystalization to separate a pair of diasteromeric salts, (S) ibuprofen- (S)- lysine and (R)- ibuprofen- (S)- lysine.

It is an object of this invention to provide a process for producing direct compressible ibuprofen which is suitable for mixing with various pharmaceutically-acceptable excipients and compression into tablets or filling capsules, by granulating commercial grade ibuprofen with a hydrophilic solvent such as water at 25° C. to 85° C., or a mixture of hydrophilic and hydrophobic solvents, or hydrophobic solvent(s), to alter the crystalline surface of the ibuprofen.

Another object of this invention is to provide a method for producing direct compressible ibuprofen particles which are suitable for mixing with various pharmaceutically acceptable excipients and compression into tablets or filling capsules, which method includes mixing 100 parts of commercially available, dry ibuprofen with 10 to 30 parts of a mixture of hydrophobic and hydrophilic solvents, wherein the crystalline surface of the ibuprofen is first dissolved by one or more hydrophobic solvents such as acetone, methyl alcohol, ethyl alcohol, isopropyl alcohol and N-propyl alcohol, in non-exclusive particular, and then recrystallize by the hydrophilic solvent component such as pharmaceutically acceptable water, to produce favorable ibuprofen dry flow characteristics.

Yet another object of this invention is to provide a method or process for producing direct compressible ibuprofen which is suitable for mixing with various pharmaceutically-acceptable excipients and compression into tablets and filling capsules, by mixing commercial grade ibuprofen with a hydrophobic organic solvent or combination of organic solvents selected from the group, acetone, methyl alcohol, ethyl alcohol, isopropyl alcohol and N-propyl alcohol, in non-exclusive particular, in a ratio of ibuprofen powder 100 parts to solvent 10 to 30 parts by weight, in which the crystalline surface of the ibuprofen is dissolved by the solvent and recrystallized slowly into an ibuprofen crystalline structure having favorable dry flow characteristics after evaporation of the solvent or solvents.

Still another object of the invention is to provide a method or process for producing direct compressible ibuprofen particles which are suitable for combination with other pharmaceutically acceptable excipients and compression into tablets or filling capsules, by mixing 100 parts of commercial grade ibuprofen with 10 to 30 parts of a hydrophilic solvent such as pharmaceutically acceptable water at a temperature in the range of from about 25° C. to about 85° C., wherein the crystalline surface of ibuprofen is then instantaneously melted and recrystallized in a mixing bed to form a desirable surface for direct compression or capsule-filling purposes.

Another object of this invention is to provide a method for producing direct compressible ibuprofen from commercially available, dry ibuprofen, which method includes mixing the dry ibuprofen with a micron size, amphorous silica gel (SiO$_2$) to facilitate coating the dry ibuprofen particles with silica gel and realizing desirable free-flowing characteristics of the coated ibuprofen particles.

Still another object of this invention is to provide a method for providing direct compressible ibuprofen particles from commercially available, dry ibuprofen, which includes coating the dry ibuprofen with either a coagulated aerosol of synthetic silica gel or a hydrophilic, fumed (pyrogenic) silica gel or micron size amorphous silica gel to facilitate coating of the flow-inhibiting crystalline structure of the dry ibuprofen into free-flowing, coated ibuprofen particles which are suitable for mixing with selected pharmaceutically acceptable excipients and direct compression into tablets or filling capsules.

SUMMARY OF THE INVENTION

These and other objects of the invention are provided in a method or process for producing direct compressible ibuprofen which is formulated in a first preferred embodiment by mixing dry, commercially available ibuprofen with heated, purified water or with water and a mixture of a pharmaceutically acceptable hydrophobic organic solvent which is miscible with water or with a hydrophobic organic solvent selected from at least one of the group, acetone, methyl alcohol, ethyl alcohol, isopropyl alcohol and N-propyl alcohol, to facilitate alteration of the crystalline ibuprofen structure from a flow-inhibiting configuration to a free-flowing configuration. In a second preferred embodiment the free-flowing ibuprofen crystalline structure is facilitated by mixing the dry, commercially available ibuprofen with micron size, amorphous silica gel (SiO$_2$) which may be in the form of a coagulated aerosol of synthetic silica or fumed silica gel, in non-exclusive particular, to facilitate free-flowing characteristics of the ibuprofen.

DESCRIPTION OF THE PREFERRED EMBODIMENTS

In a first preferred embodiment of the invention, commercial grade, dry ibuprofen is converted from a flow inhibiting, easily caking, raw product to a free-flowing, easily compressible pharmaceutical grade material by mixing the raw ibuprofen with a granulating agent. The granulating agent may include a hydrophilic solvent such as pharmaceutically acceptable, distilled or otherwise purified USP water at 25° C. to 85° C., which heated water melts at least the outer crystalline structure of the ibuprofen and alters the crystalline structure to a more free-flowing configuration. Since the melting point of the ibuprofen is about 73° C., the heated water is able to effect the desired crystalline structure change without adversely affecting the therapeutic properties of the ibuprofen. The altered, wet ibuprofen is then air dried or oven dried and screened by conventional techniques to produce a highly free-flowing, pharmaceutical grade ibuprofen which is ready for tableting or placement in capsules. Alternatively, the granulating liquid may include a mixture of a hydrophilic solvent such as purified water and one or more hydrophobic organic solvents such as acetone, methyl alcohol, ethyl alcohol, isopropyl alcohol and N-propyl alcohol, in non-exclusive particular, wherein the crystalline structure of the ibuprofen is dissolved and altered at a lower temperature. Under circumstances where both the hydrophilic and hydrophobic solvents are utilized, small amounts of hydrophobic solvent are most preferably used to partially dissolve the ibuprofen and are recrystallized by the water, thereby changing only the surface characteristics of the crystals to produce a more free-flowing product. Accordingly, the solvent is easily evaporated from the solvent-ibuprofen mixture after the surface alteration process and the resulting free-flowing ibuprofen can be air or oven dried and screened as described above, according to conventional techniques. The resulting product is then ready for mixing with selected excipients and tableting or filling capsules in conventional manner. In yet another alternative embodiment of the invention the raw, dry, commercially available ibuprofen may be mixed with one or more hydrophobic organic solvents such as acetone, methyl alcohol, ethyl alcohol, isopropyl alcohol and N-propyl alcohol, in non-exclusive particular, in the absence of water to effect the desired crystalline alteration and prepare the ibuprofen for tableting and introduction into capsules. As in the case of the hydrophilic-hydrophobic solvent combination, the hydrophobic solvent treatment as a granulating liquid is most preferably effected using small amounts of the solvent or solvents to facilitate the desired crystalline alteration and slow evaporation of the solvent or solvents for optimum drying of the altered ibuprofen product. The ibuprofen is then conventionally dried by air or in an oven, if necessary, screened and subsequently compressed into tablets with selected excipients or introduced into the capsules. It will be appreciated by those skilled in the art that under circumstances where the hydrophilic and hydrophobic solvents, as well as the hydrophobic solvent or solvents alone, are utilized to alter the crystalline structure of the ibuprofen, a preferred temperature range within which to effect the crystal-altering process is from about 20° C. to about 100° C. A more preferred temperature range within which to effect the solvent-ibuprofen mixing is from about 20° C. to about 30° C., and a most preferred temperature for treating the raw, dry, commercially available ibuprofen with the hydrophilic and hydrophobic or hydrophobic solvent or solvents is about 25° C.

In another preferred embodiment of the invention, free-flowing, direct compressible ibuprofen may be prepared by mixing commercial grade, dry ibuprofen with a micron size amorphous silica gel, or silicon dioxide, in order to coat the undesirably shaped ibuprofen particles and facilitate a more free-flowing crystalline structure. A typical formulation for the micron size amorphous silica gel is a coagulated aerosol of synthetic silica marketed as "Aerosil 200" by Degussa Corporation of Plano, Tex. The "Aerosil 200" product is known as a free-flow lubricating and release agent (FLR complex) and has been found through the investigations of this invention to exhibit good coating characteristics for adhering to and enhancing the flow properties of the ibuprofen particles.

Another silicon dioxide silica gel product which has been found in the investigations of this invention to favorably coat commercial grade, dry ibuprofen is a syloid silica gel product known as "Syloid silicas FP", manufactured by W. R. Grace Corporation of Baltimore, Maryland. The syloid silica gel product is manufactured by reacting sodium silicate with sulfuric acid and is characterized by a micron size, odorless, tasteless, amorphous white powder which is chemically inert and adheres tightly to the ibuprofen particles to change the configuration of the particles and create a more free-flowing, dry ibuprofen product. Syloid silica gels are known in the pharmaceutical industry as anti-caking agents, glidants, liquid carriers (or moisture scavengers) and dispersants. The syloid silica gels are characterized by an internal structure of sponge-like pores which imparts an extremely high adsorptive capacity and renders the powder an efficient carrier for active organic ingredients. The syloid silica gels are very efficient in absorbing moisture in the millions of internal pores, thereby preventing subsequent degradation of the ibuprofen product by excess moisture. Furthermore, the syloid silica gels also coat and separate each particle of ibuprofen to maintain the particles in a free-flowing state through the various hoppers, filling devices and machinery used in the process of creating the various solid ibuprofen dosage forms and filling capsules. It has been found that as little as 0.05% to about 1.0% of syloid silica gel by weight will maintain the particles of ibuprofen in a free-flowing condition. The syloid silica gels are typically finally-divided, chemically inert, 99.8% silica dioxide and are manufactured synthetically by a process which yields a different structure from pyrogenic, fumed silica dioxide such as "Aerosil 200". Syloid silica gels also offer superior direct compressibility properties when compared with other silicon dioxide products.

Still another variation of the silicon dioxide silica gel products which may be utilized to enhance the free-flowing characteristics of dry, commercially available ibuprofen according to the investigations of this invention is a fumed or pyrogenic silicon dioxide sold under the trademark, "Cab-O-Sil", by the Cabot Corporation of Boston, Mass. The "Cab-O-Sil" silicon dioxide product is characterized by extremely small particle size and an enormous surface area and is produced by the hydrolysis of silicon tetrachloride vapor in a flame of hydrogen and oxygen. The "Cab-O-Sil" product is compatible with ibuprofen particles to form tablets and filling of capsules, since it has been found to coat the ibuprofen particles and facilitates a better free-flowing characteristic of the particles. The "Cab-O-Sil" silica dioxide has been observed to achieve the desired freeflow function in ibuprofen through the following mechanisms: when added to dry, commercially available ibuprofen it promotes free flow by functioning as an anti-blocking and anti-friction agent. Furthermore, the sub-microscopic size of the "Cab-O-Sil" particles permits these particles to move easily between the larger particles of the ibuprofen powder, thereby lending an additional anti-friction characteristic to the normally flow-inhibiting ibuprofen crystals.

The invention will be better understood by reference to the following examples:

EXAMPLE 1

1000 grams of commercially available, dry ibuprofen purchased from Ethyl Corporation in Baton Rouge, La., was mixed in a container with 200 ml. of isopropyl alcohol at a temperature of 25° C. and the mixture was thoroughly stirred. The mixture was then allowed to air dry to evaporate the isopropyl alcohol and the resulting ibuprofen was screened through a no. 14 mesh screen to form uniform particles or granules suitable for mixing with other pharmaceutically acceptable, inert excipients preparatory to the tableting or capsule-filling process.

EXAMPLE 2

The conditions of Example 1 were duplicated with a 1:1 isopropyl alcohol and water mixture added to the dry, commercial grade ibuprofen and the mixture was effected at a temperature of 25° C. The water component was purified USP grade water and after thoroughly mixing the isopropyl alcohol and water, this solution was then added to the ibuprofen and the resulting mixture was air dried and subsequently passed through a no. 18 mesh screen. The resulting freeflowing ibuprofen was then mixed with pharmaceutically acceptable excipients for tableting and capsule-filling.

EXAMPLE 3

Purified USP grade water was heated to 85° C. and mixed in a container with dry, commercial grade ibuprofen obtained from Ethyl Corporation in Baton Rouge, La. The resulting mixture was then air dried and the ibuprofen passed through a no. 14 mesh screen and was found suitable for mixing with various excipients for tableting and capsuling.

EXAMPLE 4

The procedure of Example 1 was repeated, mixing dry, commercial ibuprofen with acetone, ethyl alcohol, methyl alcohol, isopropyl alcohol and N-propyl alcohol, respectively, in separate applications as individual hydrophobic organic ingredients and in each case the resulting ibuprofen mixture was ventilated in an oven or air dried and the dry ibuprofen was passed through a no. 14 mesh screen and found suitable for mixing with various excipients for tableting and capsuling.

EXAMPLE 5

The procedure of Example 2 was repeated, mixing dry, commercial ibuprofen with various mixtures of acetone and water, ethyl alcohol and water, methyl alcohol and water, isopropyl alcohol and water and N-propyl alcohol, respectively, and the resulting ibuprofen mixtures were oven dried at 40° C. to 60° C. to remove the respective solvent. The dried ibuprofen was passed through a no. 18 mesh screen and found suitable for mixing with various excipients for tableting and capsuling.

EXAMPLE 6

Commercial grade, dry ibuprofen was mixed in a container with "Syloid 244FP" amorphous, micron size silicon dioxide in a ratio of 10 grams of "Syloid 244FP" to 1000 grams of ibuprofen and the mixture was passed through a no. 14 mesh screen to produce a uniform, free-flowing, direct compressible powder suitable for mixing with various excipients for tableting and capsule filling. No drying was observed to be necessary.

EXAMPLE 7

Commercial grade, dry ibuprofen was mixed in a container with "Aerosil 200" amorphous, micron size, coagulated aerosol of synthetic silica in the proportions of 10 grams of "Aerosil 200" to 1000 grams of Ibuprofen and the mixture was passed through a no.14 mesh screen to produce a uniform, free-flowing, direct compressible powder suitable for mixing with various excipients for tableting and capsule filling. No drying was observed to be necessary.

EXAMPLE 8

Commercial grade, dry ibuprofen was mixed with "Cab-O-Sil" silicon dioxide in the proportions of 10 grams of Cab-O-Sil to 1000 grams of ibuprofen and the mixture was passed through a no.14 mesh screen to produce a uniform, free-flowing, direct compressible powder suitable for mixing with various excipients for tableting and capsule filling. No drying was observed to be necessary.

A primary advantage of the processes of this invention is the capacity to directly treat or coat commercially-available, dry ibuprofen in a simple, easily controlled and inexpensive manner using conventional high-shear mixers and tablet-compression and hard shell gelatin filling machines. It has been found unnecessary to add binders to the ibuprofen treated or coated according to the processes of this invention and the final ibuprofen product containing suitable excipients has been found to exhibit excellent hardness and stability over a considerable temperature range for shipping, as well as tableting purposes. However, conventional diluents such as starch, lactose and like excipients can also be added in conventional manner to the ibuprofen product of this invention for direct compression purposes.

While the preferred embodiments of this invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A process for enhancing the flow characteristics of ibuprofen, comprising the steps of granulating the ibuprofen with a hydrophilic solvent and a hydrophobic organic solvent which is miscible with said hydrophilic solvent to dissolve and modify and crystal surface of the ibuprofen and drying the ibuprofen.

2. The process of claim 1 wherein said mixing is accomplished at a temperature in the range of from about 20° C. to about 100° C.

3. The process of claim 1 wherein said hydrophilic solvent and said hydrophobic solvent are premixed in a concentration ratio of from about 1 to about 99, respectively.

4. The process of claim 1 wherein:
   (a) said hydrophilic solvent and said hydrophobic solvent are premixed in a concentration ratio of from about 0.5 to about 99.5, respectively; and
   (b) said mixing is accomplished at a temperature in the range of from about 20° C. to about 100° C.

5. The process of claim 1 wherein said hydrophilic solvent further comprises water and said hydrophobic solvent is selected from at least one of the group acetone, methyl alcohol, ethyl alcohol, isopropyl alcohol, and N-propyl alcohol.

6. The process of claim 5 wherein said mixing is accomplished at a temperature in the range of from about 20° C. to about 100° C.

7. The process of claim of claim 5 wherein said water and said hydrophobic solvent are premixed in a concentration ratio of from about 0.5 to about 99.5, respectively.

8. The process of claim 5 wherein:
   (a) said hydrophilic solvent and said hydrophobic solvent are premixed in a concentration ratio of about 1 to 1, respectively; and
   (b) said mixing is accomplished at a temperature in the range of from about 20° C. to about 85° C.

9. The process of claim 1 wherein said hydrophilic solvent further comprises water.

10. The process of claim 9 wherein said mixing is accomplished at a temperature in the range of from about 20° C. to about 100° C.

11. The process of claim 10 wherein said water and said hydrophobic solvent are premixed in a concentration ratio of from about 0.5 to about 99.5, respectively.

12. The process of claim 11 wherein said hydrophobic solvent is selected from at least one of the group, acetone, methyl alcohol, ethyl alcohol, isopropyl alcohol, and N-propyl alcohol.

13. The process of claim 1 wherein said hydrophobic solvent is selected from at least one of the group, acetone, methyl alcohol, ethyl alcohol, isopropyl alcohol, and N-propyl alcohol.

14. The process of claim 13 wherein said mixing is accomplished at a temperature in the range of from about 20° C. to about 100° C.

15. The process of claim 14 wherein said hydrophilic solvent and said hydrophobic solvent are premixed in a concentration ratio of from about 0.5 to about 99.5, respectively.

16. The process of claim 15 wherein said hydrophilic solvent is water.

17. A process for enhancing the flow characteristics of ibuprofen by altering the surface crystalline structure of the ibuprofen, comprising the steps of mixing commercially-available, substantially dry ibuprofen with a hydrophobic organic solvent and drying the surface-altered ibuprofen.

18. The process of claim 17 wherein said mixing is accomplished at a temperature in the range of from about 20° C. to about 100° C.

19. The process of claim 17 wherein said hydrophobic solvent is selected from at least one of the group, acetone, methyl alcohol, ethyl alcohol, isopropyl alcohol and N-propyl alcohol.

20. The process of claim 19 wherein said mixing is accomplished at a temperature in the range of from about 20° C. to about 100° C.

21. A process for enhancing the flow characteristics of ibuprofen by altering only the surface crystalline structure of the ibuprofen, comprising the steps of granulating commercially-available, substantially dry ibuprofen with pharmaceutically acceptable water at a temperature in the range of from about 25° centigrade to about 85° centigrade and drying the surface-altered ibuprofen.

22. The process of claim 21 wherein said mixing is accomplished at a temperature in the range of from about 40° C. to about 70° C.

23. A process for enhancing the flow characteristics of ibuprofen, comprising dry mixing and coating the ibuprofen with amorphous silica gel.

24. The process of claim 23 wherein said amorphous silica gel is added to the ibuprofen in a weight percent of from about 0.05% to about 5.0% of the weight of the ibuprofen.

25. The process of claim 23 wherein said amorphous silica gel is micron size.

26. The process of claim 23 wherein:
(a) said amorphous silica gel is added to the ibuprofen in a weight percent of from about 0.05 % to about 5.0% of the weight of the ibuprofen; and
(b) said amorphous silica gel is micron size.

27. The process of claim 23 wherein said silica gel is selected from the group, a coagulated aerosol of synthetic silica, a syloid silica gel and fumed silicon dioxide.

* * * * *